United States Patent [19]

Parkinson

[11] 3,976,891

[45] Aug. 24, 1976

[54] PHOTOELECTRIC DETECTOR FOR SMOKE OR THE LIKE

[75] Inventor: Thomas F. Parkinson, Columbia, Mo.

[73] Assignee: Electra-Tronics, Inc., Sarasota, Fla.

[22] Filed: Feb. 18, 1975

[21] Appl. No.: 550,626

[52] U.S. Cl.............................. 250/575; 250/227; 340/237 S; 356/207
[51] Int. Cl.².......................................... G01N 21/26
[58] Field of Search .......... 250/573, 574, 575, 227; 356/207, 208; 340/237 S

[56] References Cited
UNITED STATES PATENTS

| | | | |
|---|---|---|---|
| 3,447,370 | 6/1969 | Tanzman | 356/207 |
| 3,619,624 | 11/1971 | Sorenson | 250/575 |
| 3,652,850 | 3/1972 | Briggs | 356/208 |
| 3,677,652 | 7/1972 | Little | 250/573 |
| 3,772,525 | 11/1973 | Goodwin | 250/575 |
| 3,784,307 | 1/1974 | Jackson et al. | 250/575 |
| 3,805,066 | 4/1974 | Chijuma et al. | 340/237 S |
| 3,809,913 | 5/1974 | Prellwitz | 356/207 |

*Primary Examiner*—Alfred E. Smith
*Assistant Examiner*—D. C. Nelms
*Attorney, Agent, or Firm*—George H. Baldwin; Arthur G. Yeager

[57] ABSTRACT

A photoelectric detector in which partial light beam obfuscation caused by dirty windows is balanced out by providing two beams of light passed through the gaseous medium in which smoke or the like is to be detected, the beam windows being subject to substantially equal accumulation thereon over a period of time of soot or the like which causes the windows to become dirty or clouded. The windows are so spaced that the respective beams pass different distances through the smoke. The relative beam intensities as received are compared by connecting photoresponsive devices in a bridge circuit. A meter is connected to the bridge and preferably calibrated to read directly in Ringlemann numbers.

4 Claims, 8 Drawing Figures

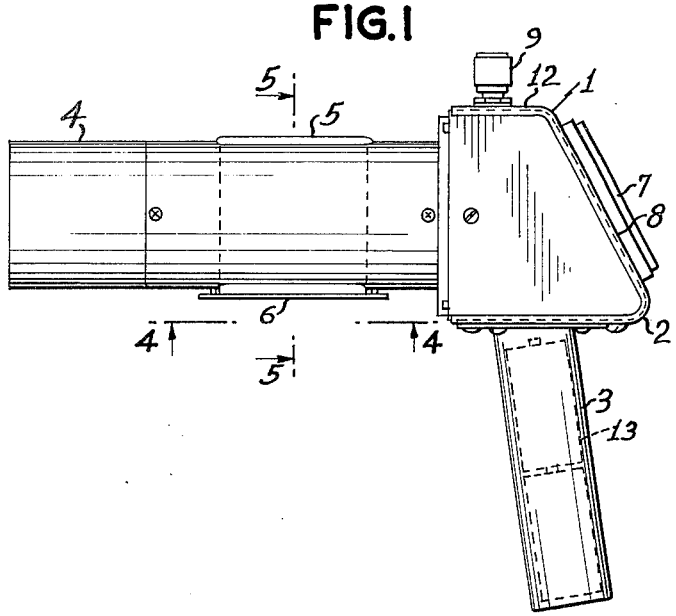
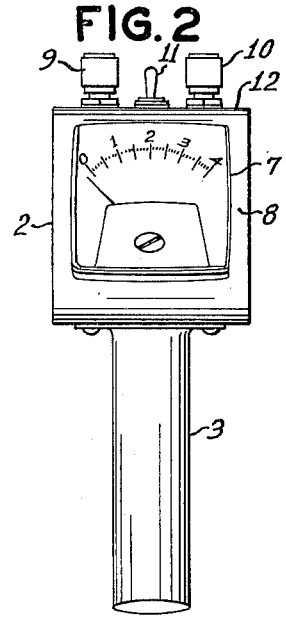
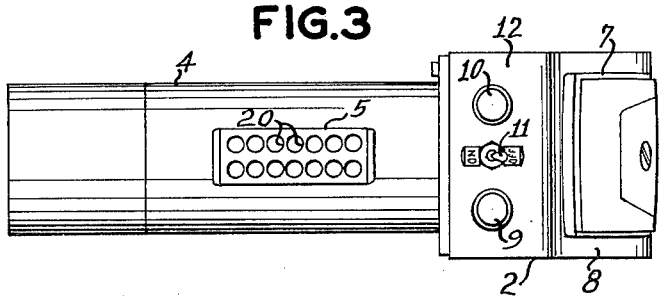
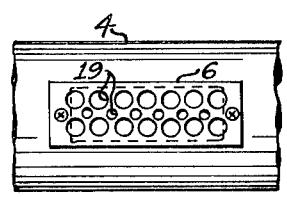
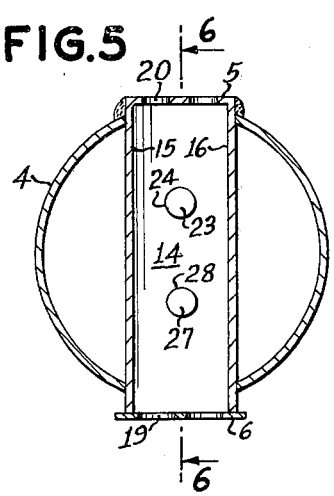
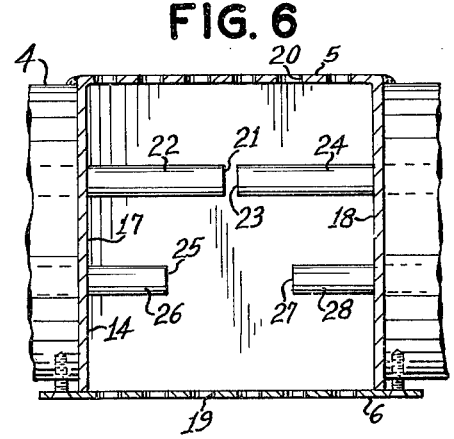

PHOTOELECTRIC DETECTOR FOR SMOKE OR THE LIKE

It has been known to pass a light beam through a fluid filled space and to measure the intensity of the beam received after it has passed through the space to detect the presence, or to measure the density, of smoke or the like in the space. U.S. Pat. Nos. 2,278,920; 2,466,696; 2,572,008; 2,666,583; 2,694,335; 2,806,148; 3,028,490; 3,111,837; 3,202,826; 3,281,597; and 3,513,319 disclose systems of this or related types, or elements useful therein, and several of these include bridge circuit means for detecting imbalance between two light beams.

A persistent problem in the operation of smoke detectors is the gradual accumulation of smoke particles or soot, or dust particles or the like on the faces of the windows which are exposed to the air or gas in which the particles to be detected are, or may be, entrained.

It is an object of the invention to provide an accurate and reliable detector for smoke or the like in which partial obfuscation of windows exposed to the gas has minimal effect on the response and calibration of the detector.

It is a further object of the invention to provide a smoke density meter of which the response is a substantially linear function of the Ringelmann number or optical absorbance of the particulate contaminants in the smoke.

The term smoke is used herein in a broad sense to include particulate contaminants dispersed in a gaseous medium, which may be air or other gases or gaseous mixtures. Thus the instrument herein disclosed is useful not only for detecting and measuring the absorption of particles in smoke from burning wood, fabrics, paper or the like, but also for measuring the density of particulate matter in internal combustion engine exhausts or of lint, dust, pollen, or the like dispersed in air.

The word "detector" as used herein is intended to encompass devices which indicate or respond to the presence or absence of smoke of predetermined density, as well as devices which provide an indication or measure of densities over a range. While air in which smoke may be present is usually such as gradually to cause the windows of a chamber through which the air passes to become dirty or clouded, similar effects may result with gases which may entrain other particles apt to accumulate on the windows, and the invention has applicability thereto.

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

FIG. 1 is a side elevational view of a smoke detector in accord with the invention;

FIG. 2 is an end elevational view thereof;

FIG. 3 is a top view thereof;

FIG. 4 is a fragmentary bottom view thereof;

FIG. 5 is a sectional view taken along line 5—5 of FIG. 1;

FIG. 6 is a sectional fragmentary view taken along line 6—6 of FIG. 5;

Figure 7:
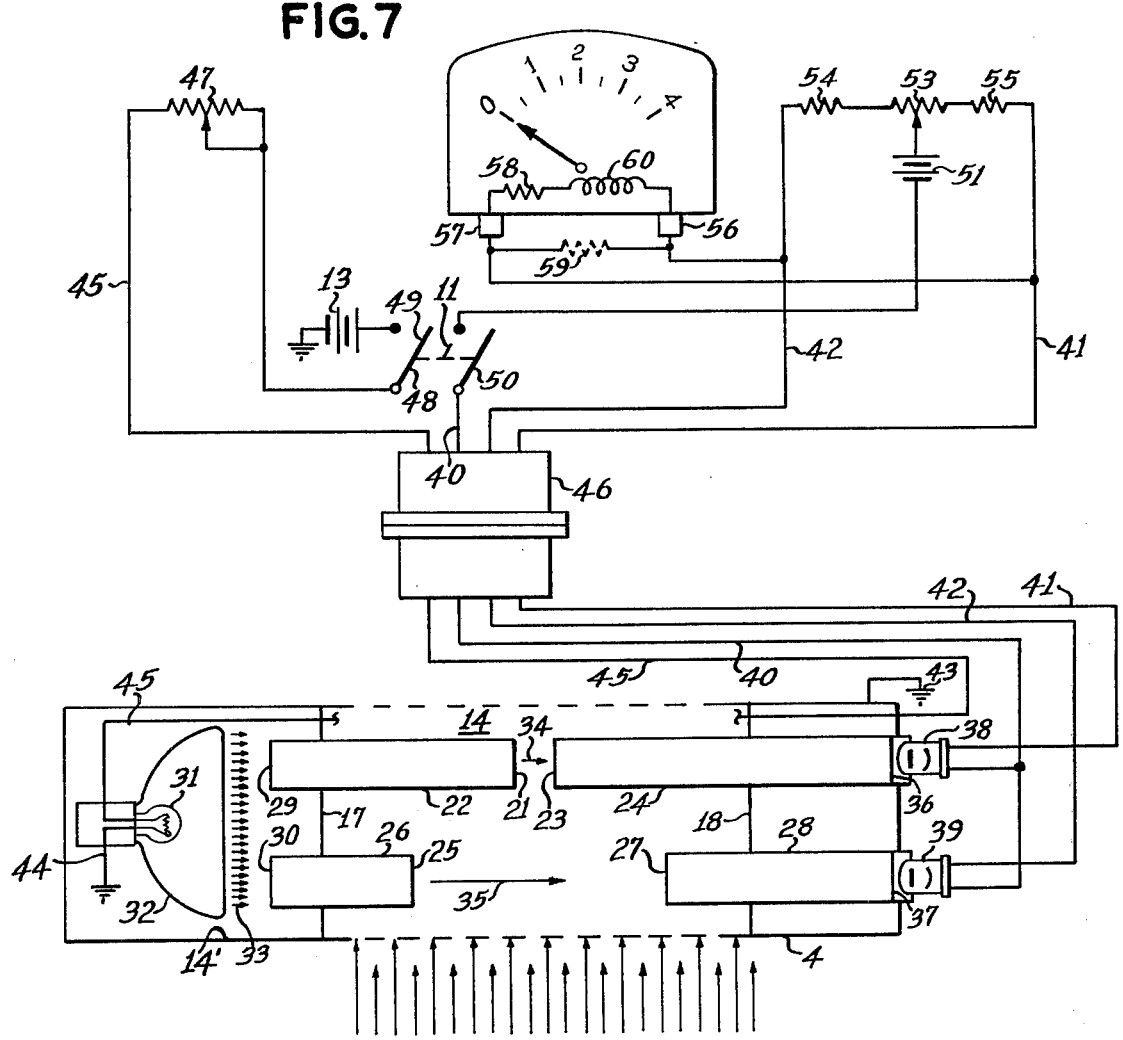
FIG. 7 is a diagrammatic view of the invention showing the arrangement of windows, light beam producing and photoelectric elements in the chamber in which smoke is to be detected, and electrical circuit portions schematically indicated.

Referring to FIGS. 1 through 4 of the drawings, the detector 1 comprises a housing 2 having a hollow handle 3 depending from the housing and with a projecting hollow cylindrical housing portion 4 provided with upper and lower gratings or apertured baffle plates 5 and 6 respectively through which the air, or other gas, may pass upwardly through the hollow interior test chamber of the housing 4.

A calibrated meter 7 is exposed on the front face 8 of the main housing portion 2, and two control knobs 9 and 10, and an on-off switch control member 11, extend upwardly from the top panel 12 of the housing. The handle portion 3 is hollow to receive batteries 13, while the housing 2 is hollow to contain the body of the switch operated by member 11, the body of meter 7, the variable resistance elements operated by knobs 9 and 10 and other electrical components of the detector.

Referring to FIGS. 5 and 6, an elongated test chamber 14 is partitioned off within housing 4 by vertical side walls 15 and 16 and by vertical end walls 17 and 18, the chamber having multiple lower entrance openings 19 provided through the apertured plate 6, and outlet openings 20 provided through the upper plate 5. The gas to be tested for the presence of smoke may rise by convection through the entrance openings 19, pass upwardly through the chamber 14 and exhaust through the openings 20 of the upper plate 5, or the gas may be forced through the chamber, such as by positioning the chamber in the stream of an engine exhaust.

A first light beam entrance window 21 into the hollow gas-filled chamber interior is formed by the inner end of a cylindrical light transmitting rod 22 and aligned therewith is an exit window 23 constituting the end of a second light transmitting rod 24. The rods are typically of methyl methacrylate resin and have the property of transmitting light therealong. A second entrance window 25 is provided by the end of a light transmitting rod 26 and an exit window 27, aligned with window 25, constitutes the inner end of light transmitting rod 28. The four rods are preferably of equal diameter, which may be about one-half inch, and are sealed through the respective walls 17 and 18 as shown. According to the invention, light is introduced into rods 22 and 26 beyond wall 17 and passes along the rods to be emitted as respective beams from the windows 21 and 25 into the gas-containing interior of the chamber. The beam from rod 22 emitted through window 21 is directed toward exit window 23 and enters rod 24 therethrough, while the beam from rod 26 emitted through window 25 enters rod 28 through its exit window 27, and the respective beams pass along through rods 24 and 28 and out through wall 18. The windows constitute planar ends of the rods, normal to the rod axis.

It will be noted that the distance between windows 21 and 23 is a fraction of the distance between windows 25 and 27. Typically, the distance from window 21 to window 23 may be 0.5 cm. and from window 25 to window 27, 5.0 cm., although the ratio between these distances may be greater than 10:1 or, with some reduction in sensitivity and calibration accuracy, as little as 2:1.

The overall arrangement of the rods and chamber 14, together with associated elements, is best understood from the diagrammatic view of FIG. 7, wherein rod 21 and rod 26 are shown to extend through wall 17 and to have outer ends 29 and 30 disposed in enclosed chamber portion 14' to receive light of equal intensity from a lamp 31 disposed in a reflector 32 which directs light in the direction of arrows 33. The light emitted from each of windows 21 and 25 passes in the form of a beam, the respective beams being represented by arrows 34 and 35, and these beams respectively pass through the spaces between the ends 21 and 23 and ends 25 and 27, and thence into and along the respective rods 24 and 28. These rods 24 and 28 extend through the smoke chamber defining wall 18 and terminate beyond chamber 14 at outer ends 36 and 37, respectively. Immediately beyond and adjacent each of these last mentioned ends is disposed a respective photo-electric device. The ends 36 and 37 and the photo-electric devices are enclosed against smoke or external light so as to receive uninterruptedly light emitted from the ends without external interference. The photoelectric devices 38 and 39, which may be Clairex type CL705L photocells, change in resistance in accord with the intensity of the light striking the cell. One terminal of each photocell is connected to a common conductor 40 while the other terminal of photocell 38 is connected to a conductor 41 and, of photocell 39, to conductor 42. The metal shell of housing portion 4 may be grounded, as represented by the ground symbol at 43, and this may be common to the metal housing 2 and housing portion 3. Lamp 31 has one grounded terminal 44 and the other terminal connected to a conductor 45. The four last mentioned conductors extend from the interior of cylindrical housing 4 into the interior of main housing 2.

The interior of the chamber 14, including the inner surfaces of baffle plates 5 and 6, as well as the cylindrical surfaces of rods 22, 24, 26 and 27, are preferably made non-reflective to the end that substantially the only light entering through the windows 23 and 27 and applied to the photo-electric cells 38 and 39 is light which has passed out of the windows 21 and 25, crossed the respective gap 34 or 35, and entered the opposite window 23 or 27.

Conductors 40, 41, 42 and 45 leading from the cylindrical housing portion 4 into the main housing 2 there connect, preferably through a separable connection plug and socket assembly 46, to the electrical components housed in housing 2 and in battery housing portion 3. Conductor 45 connects through the connector plug 46 to one terminal of a rheostat 47, of which the resistance is controlled by knob 9, and through the rheostat to one blade 48 of double pole switch 49, which is operated by manual switch knob 11. When the switch is closed, connection is completed from blade 48 to one terminal of a battery 13, which may consist of two flashlight "D" cells housed in handle 3, the other terminal of the battery being grounded. Closure of switch 49 thus completes a circuit to energize lamp 31 through current control rheostat 47.

The common connection 40 from the two photoelectric cells connects through the other pole 50 of swtich 49 to one terminal of a small battery 51, which may be a 9 volt miniature battery of the type commonly used in small personal radio receivers and which may be housed in housing 2. The other terminal of battery 51 is connected to the movable sliding contact 52 of a potentiometer 53, the slider being operated by control knob 10 previously described. Potentiometer resistance 53 is connected between resistors 54 and 55 across the meter terminals 56 and 57.

Figure 8:
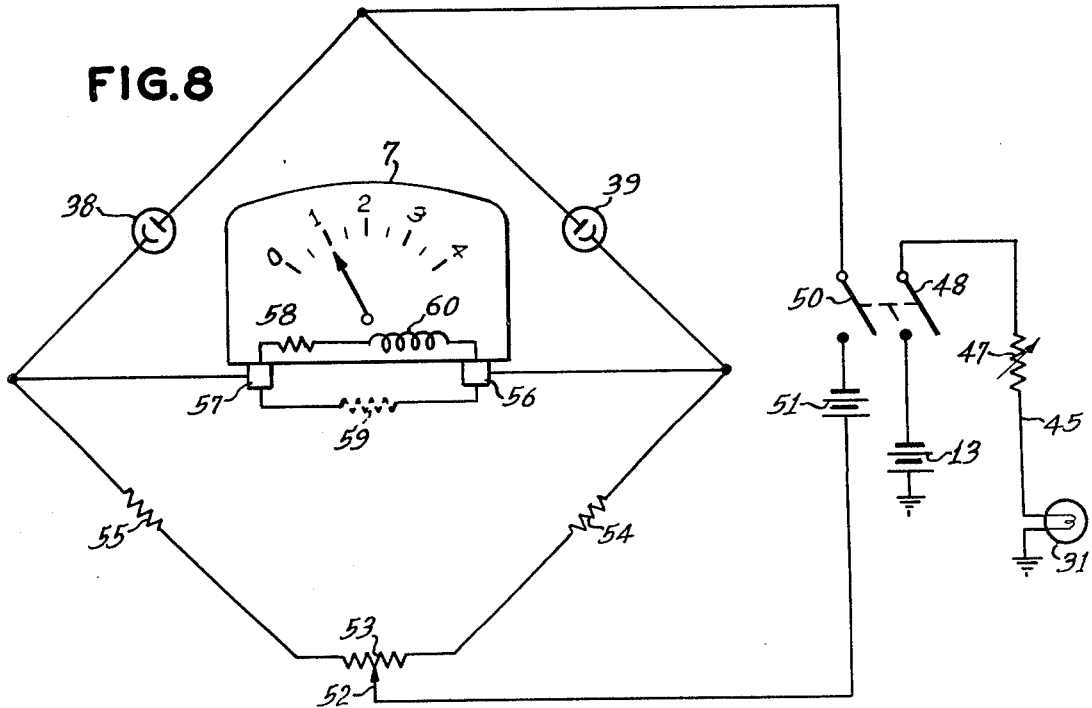
FIG. 8 is a schematic diagram of the electrical circuits of the detector.

It will be recognized from the schematic electrical circuit diagram of FIG. 8 that the photo-electric cells 38 and 39 are arranged with resistors 53, 54 and 55 in a Wheatstone bridge circuit with potentiometer 53 arranged to permit balancing of the bridge. The several circuit elements shown in this figure are identified by the same reference numerals and the circuit is otherwise as described in connection with FIG. 7.

The meter 7 may have a basic 0–20 microammeter movement with a multiplier resistor 58 of 0.1 megohms, either internally or externally disposed, and in series with the meter coil 60, thereby to provide a full scale meter deflection at 2 volts. A shunt resistor 59 may be provided, typically of 1740 ohms, to so adjust the circuit, depending upon the characteristics of the optical and electrical components of the instrument, to provide half scale meter deflection corresponding to a Ringlemann number of 2 for smoke in chamber 14.

Each of resistors 54 and 55, as well as potentiometer 53, may be of 1000 ohms, and the photo-electric cells 38 and 39 may be of a type having a resistance varying with intensity of incident light from 33 to 3300 ohms. The above identified Clairex photocells have these characteristics. Rheostat 46 may be variable from 0 to 50 ohms, battery 13 having a rating of 3 volts and lamp 31 being a 3 volt, 300 ma. flashlight bulb. When the bridge has been balanced by operation of slider 52, any subsequent unequal changes of the resistances of photocells 38 and 39 will cause a voltage to appear between terminals 56 and 57.

The meter may be originally calibrated by inserting shutters or standard neutral gray filters in the light path between rod ends or windows 25 and 27 and by selecting or adjusting meter sensitivity, such as by selection of a suitable shunt resistor as indicated in broken lines at 59, so that the meter scale may be marked to read Ringlemann numbers directly, a reading of "1" on the Ringlemann scale being the equivalent of 20% absorbance, "2" the equivalent of 40% absorbance, and "3", 60% absorbance. Once original laboratory calibration has been determined, the instrument is readily adjustable in field use by first cleaning the windows 21, 23, 25 and 27 and allowing the instrument to warm up, by closing switch 49, for a few minutes in a smoke-free environment. The meter after the warm-up period is set to zero by balancing the bridge circuit by adjusting slider 52 of potentiometer 53. A shutter proportioned to provide proper calibration is now inserted between windows 25 and 27 and rheostat 47 is adjusted to cause the meter to read "1" on the Ringlemann number scale. The zero and calibration adjustments are then repeated as necessary.

The shutter used in this field adjustment is so proportioned as to be the equivalent of approximately 18% absorption in the gap between windows 25 and 27, assuming this gap to be ten times as long as the gap between windows 21 and 23, whereby when both gaps are filled with smoke of a density, or absorbance, of 20%, or "1" on the Ringlemann scale, the meter, responding to the difference, will read "1".

The accuracy of the calibration of the instrument will be to some extent reduced by accumulation of particles, such as of the nature of soot, on the windows. Even without cleaning the windows, however, substantial quantitative accuracy of the calibration can be reestablished by the use of the shutter and repeating the manipulative steps described above to set zero meter reading, without the shutter, and the "1" reading with the shutter between windows 25 and 27. In this manner, even with windows partially occluded or clouded by deposited soot or other particles, the accuracy of the calibration is still very good, and even without such readjustment after the windows have acquired a deposit of particles, the instrument remains sensitive to changes in smoke density.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A detector responsive to smoke or the like particles present in a gas, comprising a chamber through which the gas to be tested may pass, a first pair of straight, axially aligned spaced light transmitting rods having respective confronting inner end faces within said chamber, a second pair of straight, axially aligned spaced light transmitting rods having respective confronting inner end faces within said chamber, each of said rod inner end faces being subject to gradual obfuscation by the accumulation thereon of dust or the like particles from said gas, each of said rods of each said pair having a respective outer end face at its end opposite its said inner end face and said outer end faces being disposed outwardly of said chamber, light producing means including means to pass light into one rod of each said pair through its said outer end face and through the respective said one rod and out through such inner end face thereof and thence through the gas between such face and into such other rod of the respective pair through the said confronting inner end face thereof, the distance between said confronting inner end faces of said first pair of rods being at least about twice the distance between said confronting inner end faces of said second pair of rods, each of said rod end faces being flat and perpendicular to the axis of its respective said rod, a respective photoelectric responsive means disposed adjacently opposite each said outer end face of each of said other rods for receiving the light transmitted along the respective said other rod from their said respective said inner confronting faces, and bridge circuit means for comparing the respective responses of said photoelectric responsive means.

2. The combination according to claim 1 and means to adjust the intensity of the light passed into said one rod of each said pair, said bridge circuit means comprising adjustable bridge balancing means and calibrated meter means for indicating the extent of bridge unbalance resulting from different responses of said photoelectric responsive elements.

3. The combination according to claim 1 wherein the axis of said first pair of rods is parallel to the axis of said second pair, the combined length dimension of the rods of said first pair being less than the combined length dimension of the rods of said second pair by an amount equal to the difference in said distances, and said outer end faces of said one rod of each said pair being adjacent each other and said outer end faces of said other rod of each said pair being adjacent each other.

4. A detector for detecting the presence of smoke in a gas comprising a chamber through which the gas to be tested may pass upwardly along at least one substantially uninterrupted path generally centrally of said chamber, a first and a second pair of straight, respectively axially aligned light transmitting rods, each pair including a light entrance rod and a light exit rod and each said rod having a first end face disposed outwardly of said chamber and a second end face disposed inwardly thereof, said second end faces of both said pairs being disposed in said path with such faces of each pair being disposed symmetrically on opposite sides of the center of the path, whereby all of said second end faces are substantially equally subject to gradual obfuscation by the accumulation of dust or the like particles thereon, each said end face being planar and normal to the axis of the respective said rod, the distance between the said second end faces of said first pair of rods being at least twice the distance between said second end faces of said second pair of rods, light source means outwardly of said chamber including means to direct light into said light entrance rod of each said pair through its respective said first end face, a respective photoelectric responsive element outwardly of said chamber adjacent and alignedly opposite said first end face of each said light exit rod, and bridge circuit means for comparing the respective reponses of said photoelectric responsive elements.

* * * * *